United States Patent [19]
Edwards

[11] Patent Number: 5,519,380
[45] Date of Patent: May 21, 1996

[54] PERSONAL MONITORING SYSTEM AND METHOD

[75] Inventor: Donald A. Edwards, Mequon, Wis.

[73] Assignee: Guardian Electronics, Inc., Mequon, Wis.

[21] Appl. No.: 334,525

[22] Filed: Nov. 4, 1994

[51] Int. Cl.$^6$ ................................................ G08B 23/00
[52] U.S. Cl. .................... 340/572; 340/573; 340/539; 340/825.49
[58] Field of Search ................................. 340/572, 573, 340/539, 531, 825.49

[56] References Cited

U.S. PATENT DOCUMENTS

| | | | |
|---|---|---|---|
| 4,675,656 | 6/1987 | Narcisse | 340/539 |
| 4,736,196 | 4/1988 | McMahon et al. | 340/573 |
| 4,814,751 | 3/1989 | Hawkins et al. | 340/573 |
| 4,907,845 | 3/1990 | Wood | 340/573 |
| 4,952,928 | 8/1990 | Carroll | 340/539 |
| 4,980,671 | 12/1990 | McCurdy | 340/539 |
| 5,086,290 | 2/1992 | Murray et al. | 340/539 |
| 5,115,223 | 5/1992 | Moody | 340/573 |
| 5,115,224 | 5/1992 | Kostusiak | 340/539 |
| 5,119,072 | 6/1992 | Hemingway | 340/573 |
| 5,223,816 | 6/1993 | Levinson | 340/539 |
| 5,289,163 | 2/1994 | Perez | 340/539 |

OTHER PUBLICATIONS

"Wander Watch ALERT 24" Home Care and Long Term Care Advertising Brochure.

Primary Examiner—John K. Peng
Assistant Examiner—Albert K. Wong
Attorney, Agent, or Firm—Nilles & Nilles

[57] ABSTRACT

First and second bed monitoring systems are usable in a home and in a healthcare institution, respectively, and reliably detect an attempted departure from a bed or the like by a monitored person before the monitored person's feet ever touch the floor. Both monitoring systems generate an RF signal field or disabling signal encompassing a designated volume in the vicinity of the bed and produce an alarm signal whenever an ankle bracelet or some other device worn by the monitored person moves outside of the monitored volume. The alarm signal may be generated either at the bed or at a remote location, and the alarm may be sounded either at the remote location, at the bed, or even transmitted to a nurse's station or the like. A home/area monitoring system is also provided and generates an alarm signal whenever the signal from a user worn bracelet transmitter falls below a threshold strength indicating that the user has moved beyond a "safe" area. The caregiver can easily switch the device from "HOME" to "AREA" settings and can adjust the controller to have multiple ranges within the same setting, thus varying the size of the "safe" area. Preferably, the home/area monitored system has a bed monitoring system built in to permit continued monitoring if the monitored person's condition deteriorates or if he or she starts wandering from bed.

23 Claims, 14 Drawing Sheets

PERSONAL MONITORING SYSTEM AND METHOD

BACKGROUND OF THE INVENTION

1. Field of the Invention

The invention relates to monitoring systems and, more particularly, to systems which (1) can monitor the activities of persons with dementia, small children, or any other persons who are incapacitated and/or whose activities must be monitored on a more or less continuous basis and which (2) can help a caregiver monitor a person's presence in a bed, room, home and/or other indoor or outdoor area.

2. Discussion of the Related Art

As the population ages, there have been an increasing number of people who have dementia, disorientation or who require home care. Nursing homes and institutions have the capacity to handle only a small percentage of the people requiring care. The escalating costs of health care combined with the desire of most people to remain at home has put many people in the caregiving situation. The caregiver must constantly watch the person being cared for and is subject to severe psychological stress, physical deterioration, burnout and even premature death. There is a need to help these caregivers monitor their charges to enable them to reduce stress levels, enjoy a good night's sleep and have more peace of mind knowing that the monitored person is in a safe environment.

In addition, hospitals, subacute care centers, nursing homes, hospices and other healthcare institutions are charged with caring for the elderly with dementia or people of any age who are disoriented. Many of these patients attempt to leave a bed without realizing their condition or the potential for injury. Bed falls are a major concern to healthcare staff, and the escalating costs of injury, falls and monitoring time add significantly to an institution's cost and staff stress.

Bed falls can be prevented only by strapping the patients in their beds or otherwise rendering egress impossible. Such techniques are generally not readily adaptable for use with patients of radically different sizes and weight, are at best uncomfortable for the patient, and at worst are demeaning and may result in patient injury. There is thus a need for healthcare institutions to improve the safety of their facility, reduce the costs associated with bed falls, and reduce staff stress while at the same time maintaining patient comfort and dignity. There is also a major need to be able to monitor patients of all sizes and weights, to provide immediate detection and alarm in the event of bed fall or attempted egress, and to reduce the number of nuisance alarms.

Various devices have been proposed to monitor a person's presence in bed. Such devices typically employ a weight sensor which disables an alarm signal when compressed and spring back to their original position to permit the generation of an alarm when the person's weight is removed from the sensor. These devices exhibit several drawbacks and disadvantages. First, they are unacceptable for use with frail or young persons weighing less than 100 pounds because such patients are not sufficiently heavy to compress the sensing device and thus cannot disable the alarm signal. They also may be unacceptable for extremely heavy persons because such persons may permanently compress the sensor, thus preventing an alarm signal from being generated when the person leaves the bed. Such devices are also notoriously unreliable, produce a high number of false or "nuisance" alarms, and must be frequently repaired. These devices also often fail without alarming. Finally, such devices are incapable of generating an alarm signal until the patient has actually left the bed, thus preventing the caregiver from being alerted of an attempted egress. A need has therefore arisen to provide a monitoring device usable in a bed or another location in which the monitored person is relatively stationary for extended periods of time.

Monitoring is also required for small children or persons with dementia who still retain significant mobility. One such monitoring system, disclosed in U.S. Pat. No. 4,814,751 to Hawkins et al., monitors the strength of a signal emitted by a transmitter worn by the user and generates an alarm when this signal drops below a threshold strength, indicating that the user has left a "safe" area. The effectiveness of this and other, similar devices is typically limited by the fact that the range of such devices is fixed and thus cannot be adapted to different conditions, e.g., from use within a home to use in a larger area such as a yard or picnic area. Such devices are also prone to nuisance alarms because they cannot differentiate between a true alarm condition and a condition in which the person being monitored leaves the monitored area for only a very short time or in which the signal is blocked or interfered with for a short time. Even those systems which are capable of reducing the number of nuisance alarms are not adjustable for a particular caregiver's preference. In addition, no known systems of this type are capable of also operating as a bed monitoring system, thus requiring the caregiver to purchase separate systems for monitoring an area while the patient is still ambulatory and for subsequent monitoring a bed of the monitored person's condition deteriorates.

OBJECTS AND SUMMARY OF THE INVENTION

It is therefore an object of the invention to provide a bed monitoring system which is usable by non-ambulatory persons of all sizes and weights and which does not require that the person being monitored actually leave the bed before generating an alarm system. "Non-ambulatory," as used herein, is not limited to persons incapable of walking. Rather, a "non-ambulatory" person is one who is in a bed, chair or another confined volume and who is not expected to walk or otherwise move from that volume during the monitoring period.

Another object of the invention is to provide a home caregiver with a remote alarm so he or she can be in another location within the home, in the yard or even outside the defined area.

Another object is to provide a safer and more reliable device for monitoring a small or frail person with a weight below 100 lbs and to do so giving the caregiver maximum time to appropriately respond.

Another object is to provide a monitoring device that is easy to use for the elderly, without special programming or wiring, and which significantly reduces nuisance alarms caused, e.g., by tossing or turning in bed.

Yet another object of the invention is to provide healthcare institutional staff with electronic monitoring help in detecting a patient's attempted bed departure.

Another object of the invention is to provide such staff with an immediate signal so that they can respond appropriately in the fastest possible manner to an attempted egress.

In accordance with a first aspect of the invention, these and other objects are achieved by providing a monitoring system comprising a first transmitter which generates a first, RF signal forming a signal field a portion of which is above a designated strength and encompasses a designated volume, a first receiver capable of receiving the first signal, and a second transmitter which is coupled to the first receiver and which transmits a second signal except when the first receiver receives a signal above the designated strength. Also provided are a second receiver which detects the presence or absence of the second signal and an alarm generator which is coupled to the second receiver and which generates an alarm signal in the presence of the second signal.

In order to maximize reliability and versatility, the first transmitter preferably comprises a generally planar primary antenna formed from a plurality of interconnected wire loops mounted on a flat sheet. An adjustable signal generator is preferably connected to the primary antenna and is operable to vary the designated volume by varying the source strength of the first signal.

When used in the home, the system preferably includes (1) a control module in which is mounted the signal generator and (2) a controller which is located remote from the signal generator and in which is mounted the second receiver and the alarm generator. The second transmitter in this instance transmits the second signal immediately and then at intervals of greater than 10 seconds. This permits the caregiver to be located remote from the control module and to disregard what are perceived to be nuisance alarms, thereby maximizing caregiver freedom.

Yet another object of the invention is to provide healthcare institutional staff with electronic monitoring help in detecting a patient's attempted bed departure.

Another object of the invention is to provide such staff with an immediate signal so that they can respond appropriately in the fastest possible manner to an attempted egress.

These additional objects are achieved by combining the signal generator, the second receiver, and the alarm generator in a single controller located adjacent the first antenna. This system transmits the second signal at less than 1 second intervals, thereby resulting in nearly instantaneous and continuous generation of an alarm signal in the event of an attempted egress. Means, located in the controller, are also preferably provided for transmitting the alarm signal to a nurse's call device.

Another object of the invention is to provide a method of monitoring a person in a bed or another generally fixed location having at least some of the attributes of the system described above.

In accordance with yet another aspect of the invention, this object is achieved by providing a method comprising detecting whether or not a receiver is located in a designated volume, transmitting a signal only when the receiver is located outside of the designated volume, and generating an alarm signal only in the presence of the signal.

Yet another object of the invention is to provide a portable, low cost area monitoring system which is more versatile and reliable than heretofore known systems.

In accordance with yet another aspect of the invention, this object is achieved by providing a monitoring system comprising a transmitter which is worn by a person being monitored and which transmits a first signal, a receiver which receives the first signal, and an alarm generator which is coupled to the receiver and which generates an alarm signal whenever the first signal as received by the receiver falls below a threshold. In order to increase the versatility of the device, means are provided for varying the threshold within a designated range of strengths and for selecting one of multiple strength ranges.

The system preferably reduces the number of nuisance alarms by permitting the caregiver to program the system to prevent the triggering autodialer timers or the like unless the alarm signal has continued unabated. At the same time, an audible or visual alarm is generated at the controller to apprise the caregiver that an alarm signal has been generated. In this case, the system further comprises means for transmitting the alarm signal to a first alarm immediately when the first signal as received by the receiver drops below the threshold and for transmitting the alarm signal to an autodialer timer only when the first signal as received by the receiver drops below the threshold for a designated period of time.

Yet another object of the invention is to provide an area monitoring system having one or more of the characteristics discussed above and also being capable of operating as a bed monitoring system, thus enabling the product's continued use as dementia progresses or as a monitored person becomes less ambulatory or starts wandering away from bed.

This object is achieved by providing an area monitoring systems having at least the essential characteristics described above and further comprising a primary antenna which transmits a signal forming a field a portion of which is above a designated strength and encompasses a designated volume, the transmitter transmitting the first signal only when the transmitter is located outside of the designated volume. Means are also provided for switching the system from a first operational state in which the alarm generator is capable of generating the alarm signal only in the presence of the first signal to a second operational state in which the alarm generator is capable of generating the alarm signal whenever the first signal drops below the threshold.

Other objects, features, and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made from the scope of the present invention without departing from the spirit thereof and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENTS

1. Resume

Pursuant to the invention, first and second bed monitoring systems are provided for home and healthcare institution use, respectively, and reliably detect an attempted departure from a bed or the like by a monitored person before the monitored person's feet ever touch the floor. Both monitoring systems generate an RF signal field or disabling signal encompassing a designated volume in the vicinity of the bed and produce an alarm signal whenever an ankle bracelet or some other device worn by the monitored person moves outside of the monitored volume. The alarm signal may be generated either at the bed or at a remote location, and the alarm may be sounded either at the remote location, at the bed, or even transmitted to a nurse's station or the like. A home/area monitoring system is also provided and generates an alarm signal whenever the signal from a user worn bracelet transmitter falls below a threshold strength indicating that the user has moved beyond a "safe" area. The caregiver can easily switch the device from "HOME" to "AREA" settings and can adjust the controller to have multiple ranges within the same setting, thus varying the size of the "safe" area. Preferably, the home/area monitoring system has a bed monitoring system built in to permit continued monitoring if the monitored person's condition deteriorates of if he or she starts wandering away from bed.

2. Bed Monitoring Systems

Referring initially to FIGS. 1–9 and 10–13, first (FIGS. 1–9) and second (FIGS. 10–13) bed monitoring systems 20 and 220 are illustrated for use in a home environment and in a healthcare institution environment, respectively. Both systems establish an invisible, radio frequency (RF) field "net" or volume around the lower half of the bed or other structure on which the system is employed and generate an alarm signal whenever an ankle bracelet worn by the monitored person moves outside of the net and thus detect an attempted egress before the monitored person's feet touch the floor. Because the volume or net extends a substantial distance above the bed, the monitored person can toss and turn or otherwise move freely within the net without activating the alarm. Both systems are wireless and portable. Operation of both systems is such that nuisance alarms are minimized while reliability is enhanced as compared to previously known systems. Each system can also be adjusted to accommodate the size or relative mobility of the individual person being monitored. Each of these systems will now be discussed in turn.

A. Home Bed Monitoring System

Figure 1:
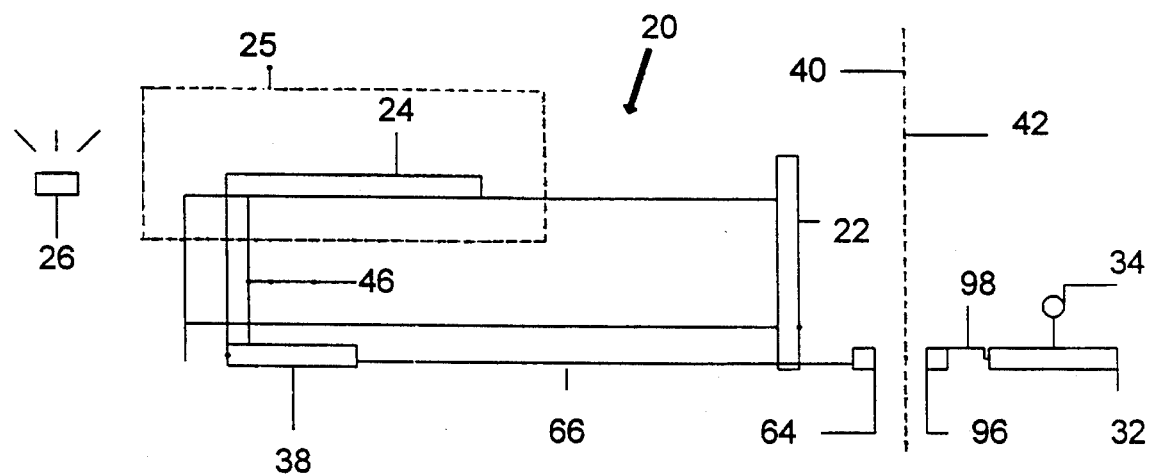
FIG. 1 schematically represents a bed monitoring system constructed in accordance with a first embodiment of the invention and designed primarily for home use.
Figure 2:
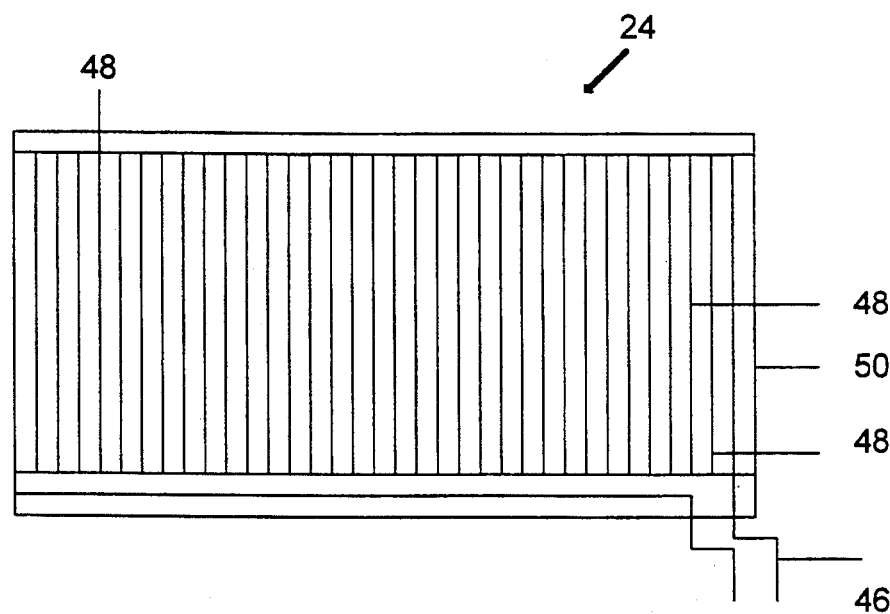
FIG. 2 is a partially schematic top plan view of the first or primary antenna of the monitoring system of FIG. 1.
Figure 3:
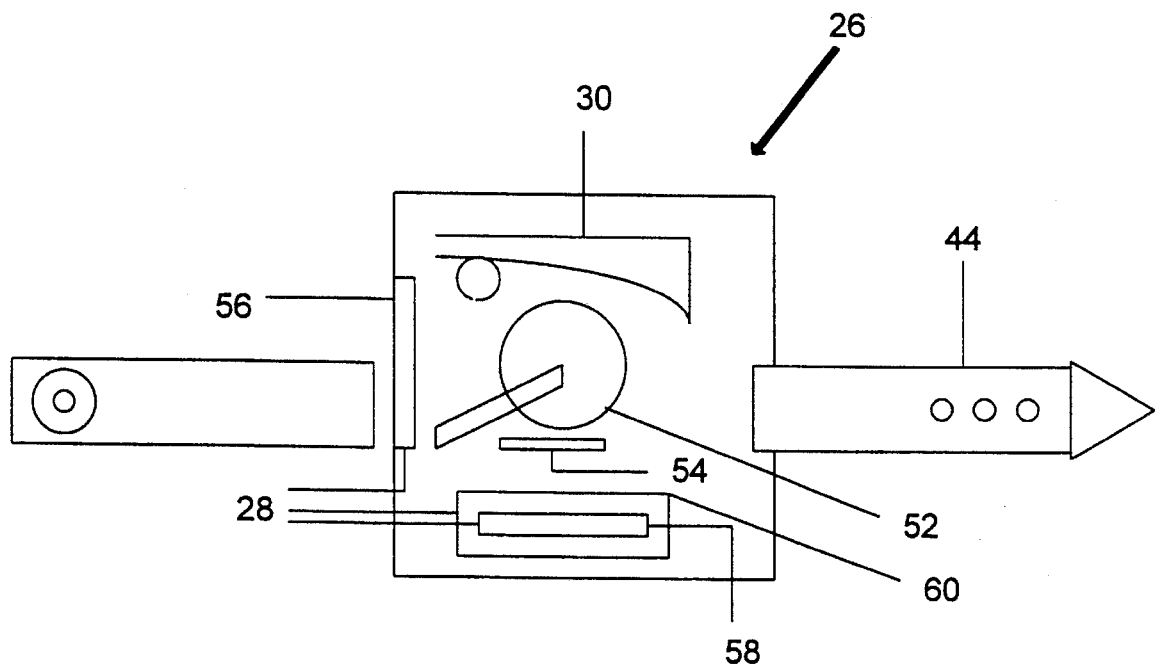
FIG. 3 is a partially schematic top plan view of the bracelet and bracelet module of the monitoring system of FIG. 1.
Figure 4:
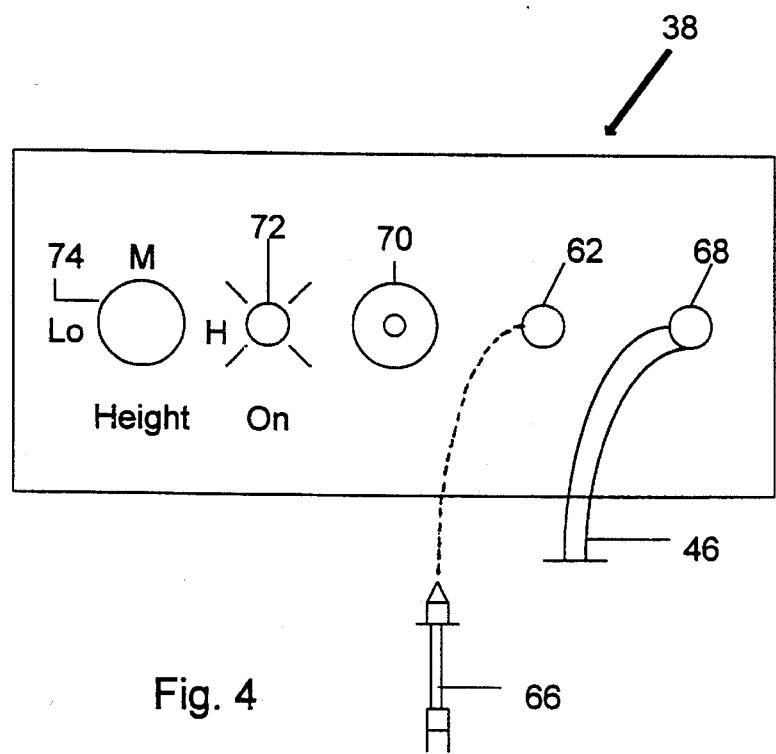
FIG. 4 is a partially schematic top plan view of the control module of the monitoring system of FIG. 1.
Figure 5:
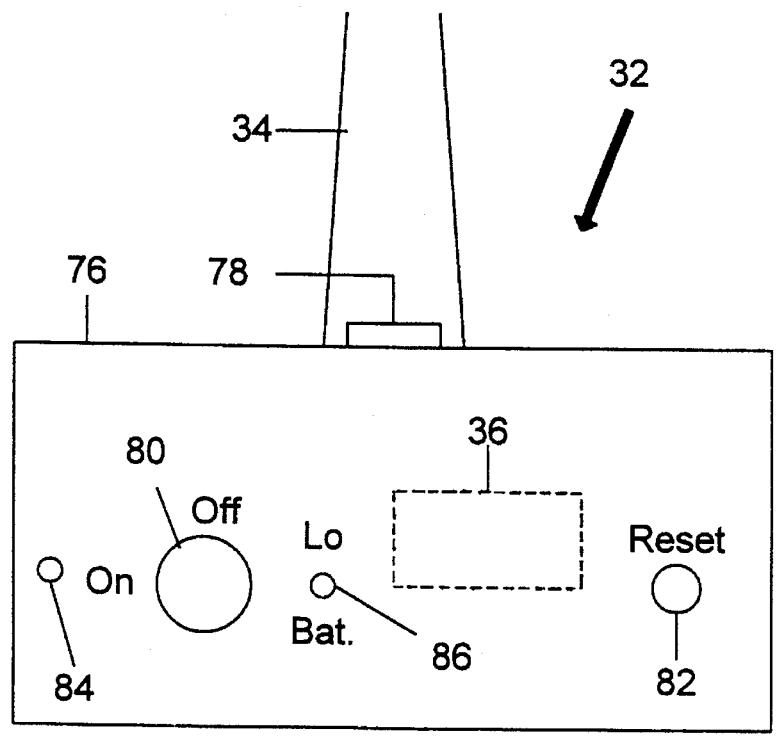
FIG. 5 is a partially schematic front elevation view of the controller of the monitoring system of FIG. 1.
Figure 6:
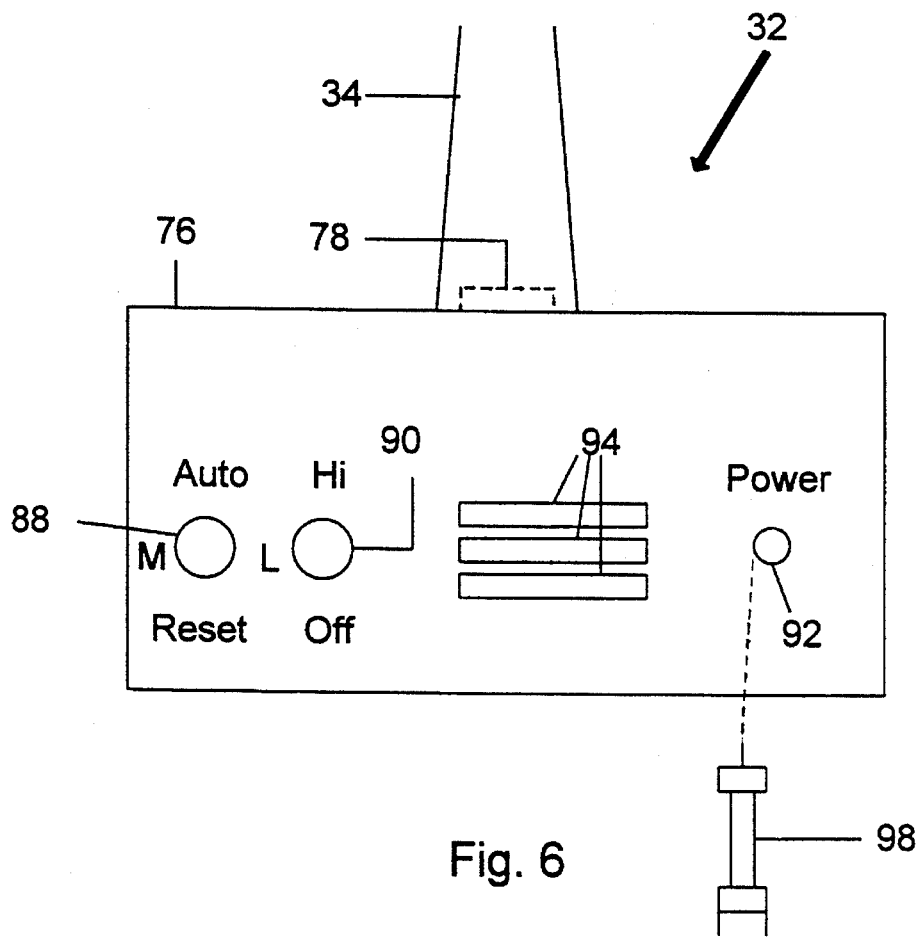
FIG. 6 is a partially schematic rear elevation view of the controller of FIG. 5.

Referring to FIGS. 1–9 and initially to FIG. 1 in particular, a home monitoring system 20 is illustrated which is designed to sound an alarm when the monitored non-ambulatory person attempts to leave a bed 22 "Non-ambulatory," as used herein, is not limited to persons incapable of walking. Rather, a "non-ambulatory" person is one who is in a bed, chair or another confined volume and who is not expected to walk or otherwise move from that volume during the monitoring period System 20 includes: a first transmitter or primary antenna 24; a bracelet module 26 which is worn by the monitored person and in which is mounted a first receiver 28 and a second or bracelet transmitter 30; and a controller 32 in which is mounted a second receiver 34 and an internal alarm generator 36 (FIG. 5). Operation of the primary antenna 24 is controlled by a control module 38 located, e.g., under the bed 22 or on an end table beside the bed. The controller 32 is not physically connected to any other components of the system 20 and thus may be located in a second room 42 remote from a first room 40 in which the bed 22 is located, thus giving the caregiver considerable freedom of movement.

The first transmitter or primary antenna 24 is designed to generate an RF signal a threshold strength of which as detected by the bracelet receiver 28 encompasses a net or volume 25 which a designated part of the monitored person's anatomy would not leave unless the person is attempting to leave the bed or is in danger of falling out of the bed. Antenna 24 operates at low power, preferably 9 volt, to maximize safety. In addition, the frequency of the signal from primary antenna 24 is relatively low, on the order of 150 khz, to assure penetration through the mattress and/or mattress pad while providing the relatively small signal field volume 25 extending one to four feet above the bed 22. The primary antenna 24 thus in effect transmits a disabling signal preventing operation of bracelet transmitter 30. The primary antenna 24 is preferably located near the foot of the bed and encompasses an area that the person's feet normally would not leave, thereby permitting the bracelet module 26 to be mounted on an ankle bracelet 44. Primary antenna 24 receives energizing current from the control module 38 via a suitable cord 46 and is formed from a plurality of interconnected flexible wire loops 48 mounted on a flat sheet or panel 50. Primary antenna 24 is thus relatively planar and is sufficiently thin to be placed underneath the mattress pad, between the mattress and the box spring, or at another location in which it does not provide discomfort to the person being monitored and yet is capable of generating the desired field.

It should be noted that, particularly in hospitals or other environments in which beds with metal side bars are used, the bed can help shape the volume 25 to aid in early detection of attempted egress. That is, the shape of the volume tends to be generally semi-spherical, propagating both significantly above and significantly beside and even below the primary antenna 24. However, the metal sidebars tend to limit the propagation of the signal field away from the side of the bed 22 such that bracelet module 26 leaves the volume 25 as soon as the monitored person sits up and swings his or her legs over the edge of the bed.

Referring now to FIGS. 1 and 3, bracelet 44 is relatively short and flexible so as not to provide discomfort to the monitored person and receives the bracelet module 26 in which is disposed a receiving antenna array forming the first receiver 28, a transmitting antenna forming the second or bracelet transmitter 30, a circuit assembly (not shown), and a battery 52. The circuit assembly may comprise any well-known analog and/or digital structure capable of performing the functions discussed below in connection with FIG. 7. The first receiver 28 comprises an array of three antennas 56, 58, and 60 attuned to the X, Y, and Z axes, respectively, and each capable of detecting the 150 khz signal from the primary antenna 24. The antennas 56, 58, 60 cooperate with one another and with the internal circuitry of the bracelet module 26 so as to detect the presence of a field signal generated by the primary antenna 24 above a designated threshold defining the borders of the designated volume 25 and to trigger operation of the transmitter 30 whenever the first receiver 28 moves outside of the volume 25. Use of three receiving antennas 56, 58, and 60 assures detection of the bracelet module 30 within the volume 25 regardless the orientation of the bracelet 44. This sharply reduces nuisance alarms which could otherwise be caused by normal movement of the monitored person within the volume 25. The second or bracelet transmitter 30 preferably transmits at a relatively high frequency (about 315 khz) as compared to the 150 mhz primary antenna frequency signal so as to have an increased range up to 200 feet, thus permitting the controller 32 to be placed in any room in the home or even in an adjacent area outside the house.

The control module 38 is designed to supply energizing current to the primary antenna 24 and to permit the power supply to the primary antenna 24 to be manually adjusted, thereby permitting the height of the detectable signal field to be adjusted from about one to about four feet above the primary antenna 24 to thereby vary the size of volume 25 so as to meet the needs of users of varying sizes and mobility. Referring to FIGS. 1 and 4, control module 38 has a power inlet jack 62 connected to an external AC power source 64 via a cord 66, and an outlet jack 68 connected to the inlet of the primary antenna 24 via cord 46. Also provided on the module 38 are a power switch 70, a POWER ON or PILOT LED indicator 72, and a field height control dial 74 which can be manually adjusted to vary the current supplied to the primary antenna 24. The internal circuitry required to vary the supply of current to the antenna 24 upon manipulation of the dial 74 is, per se, well known and will not be described in further detail. A backup power supply in the form of a battery (not shown) is preferably provided in the control module 38 to assure the delivery of power to the primary antenna 24 in the event of a power failure.

Referring to FIGS. 4 and 5, controller 32 comprises a casing 76 having the second receiver or antenna 34 and an alarm light 78 mounted on the upper surface thereof and having the alarm generator 36 disposed therein in the form of circuitry readily designed and constructed by those skilled in the art. A power switch 80, reset button 82, POWER ON LED indicator 84, and LOW BATTERY LED indicator 86 are provided on the front face of the casing 76. Provided on the rear face of the casing 76 are a reset mode select dial 88, an audible alarm select dial 90, a power output jack 92, and a plurality of vent holes 94. The reset mode select dial 88 permits the device to be operated in either manual reset or auto reset mode, thereby enabling or disabling operation of the manual reset switch 82. The audible alarm select dial 90 can be used to turn the audible alarm (not shown) off and on and to adjust the volume of the alarm. The power output jack 92 is connected to an external AC power source 96 by a cord 98, but an internal backup battery is also provided to maintain operation in the event of a power failure or for remote portable operation.

Figure 7:
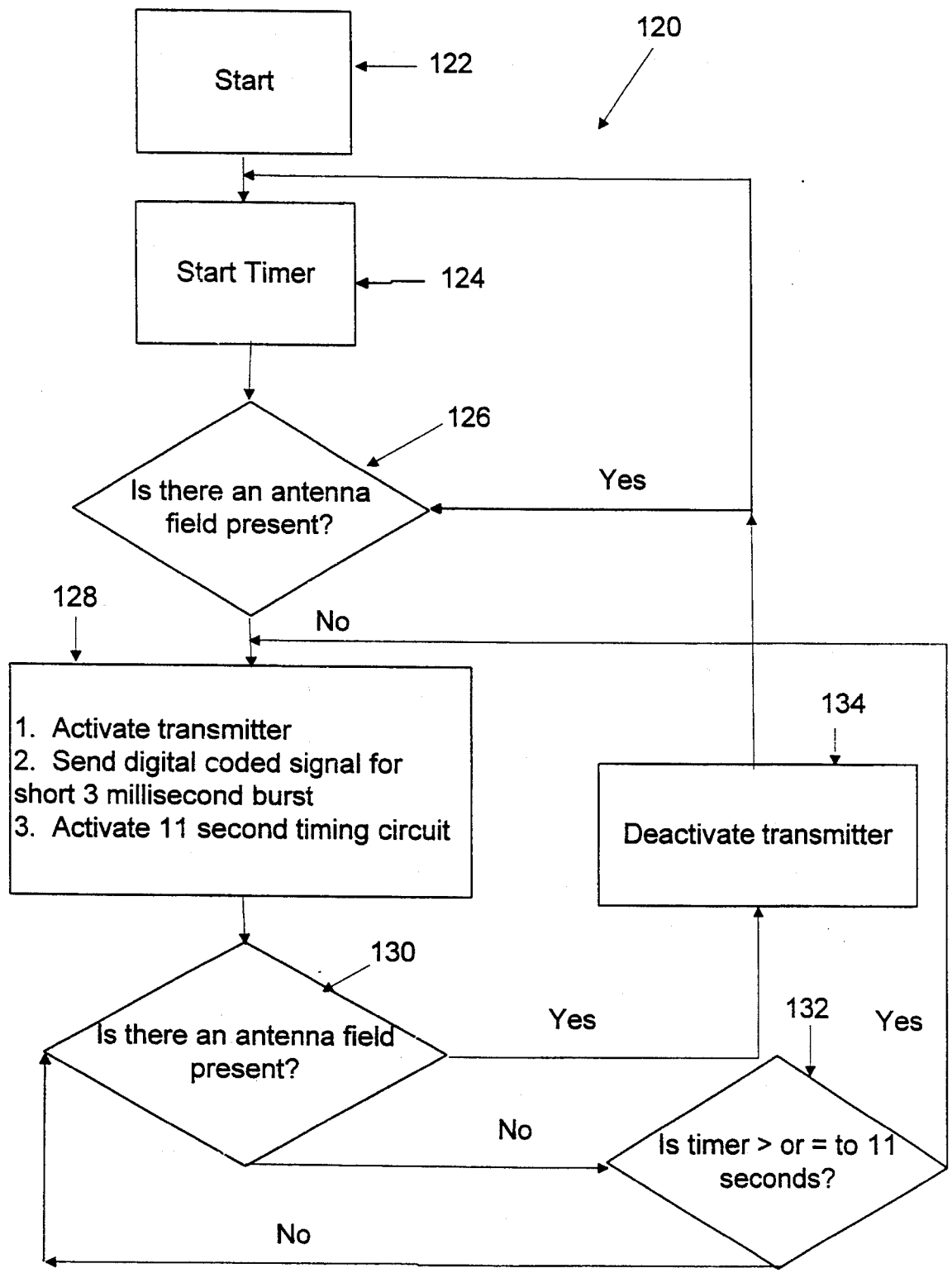
FIG. 7 is a flow chart of the operation of the internal circuitry of the bracelet module of FIG. 3.
Figure 8:
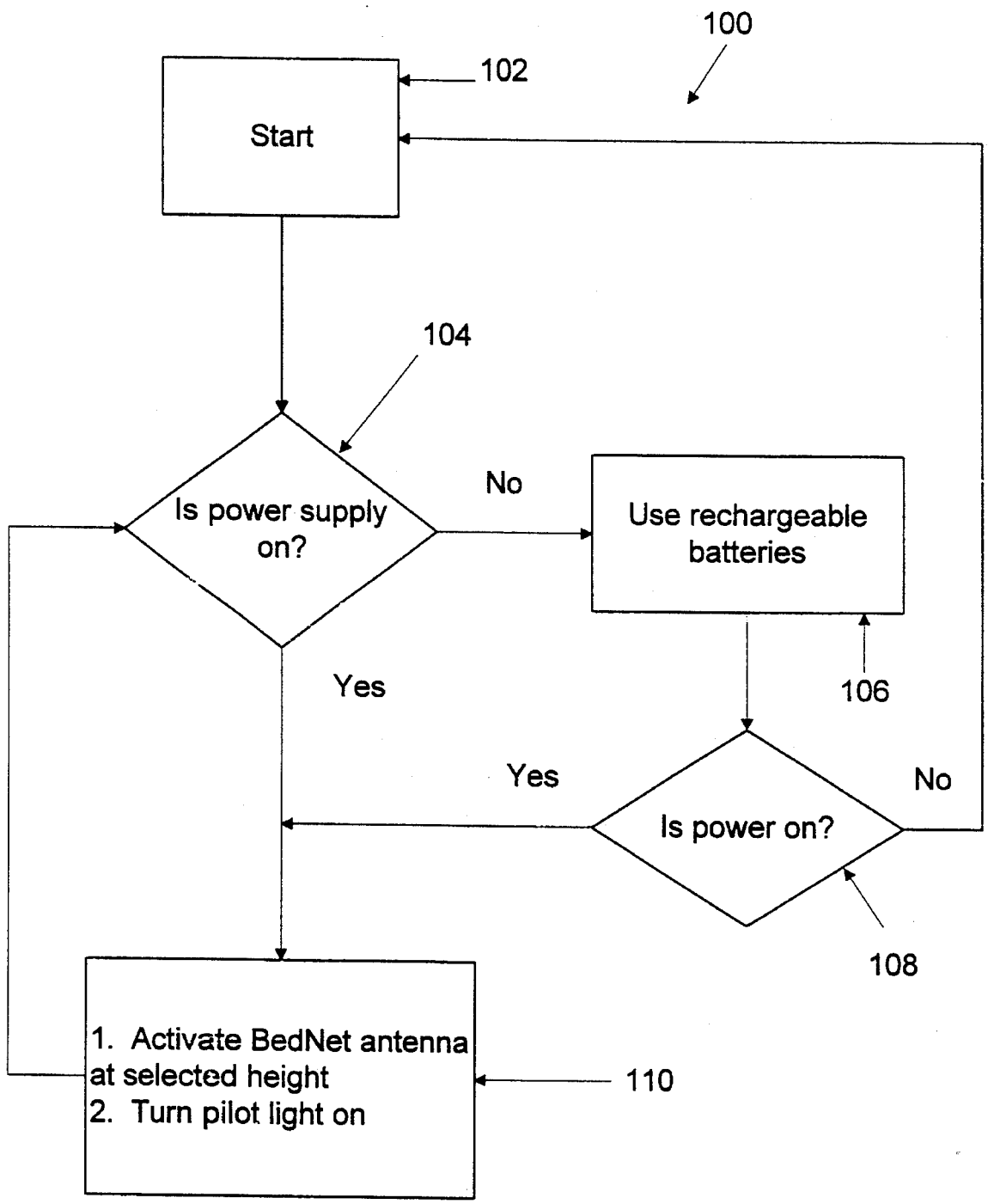
FIG. 8 is a flow chart of the operation of the internal circuitry of the control module of FIG. 4.
Figure 9A:
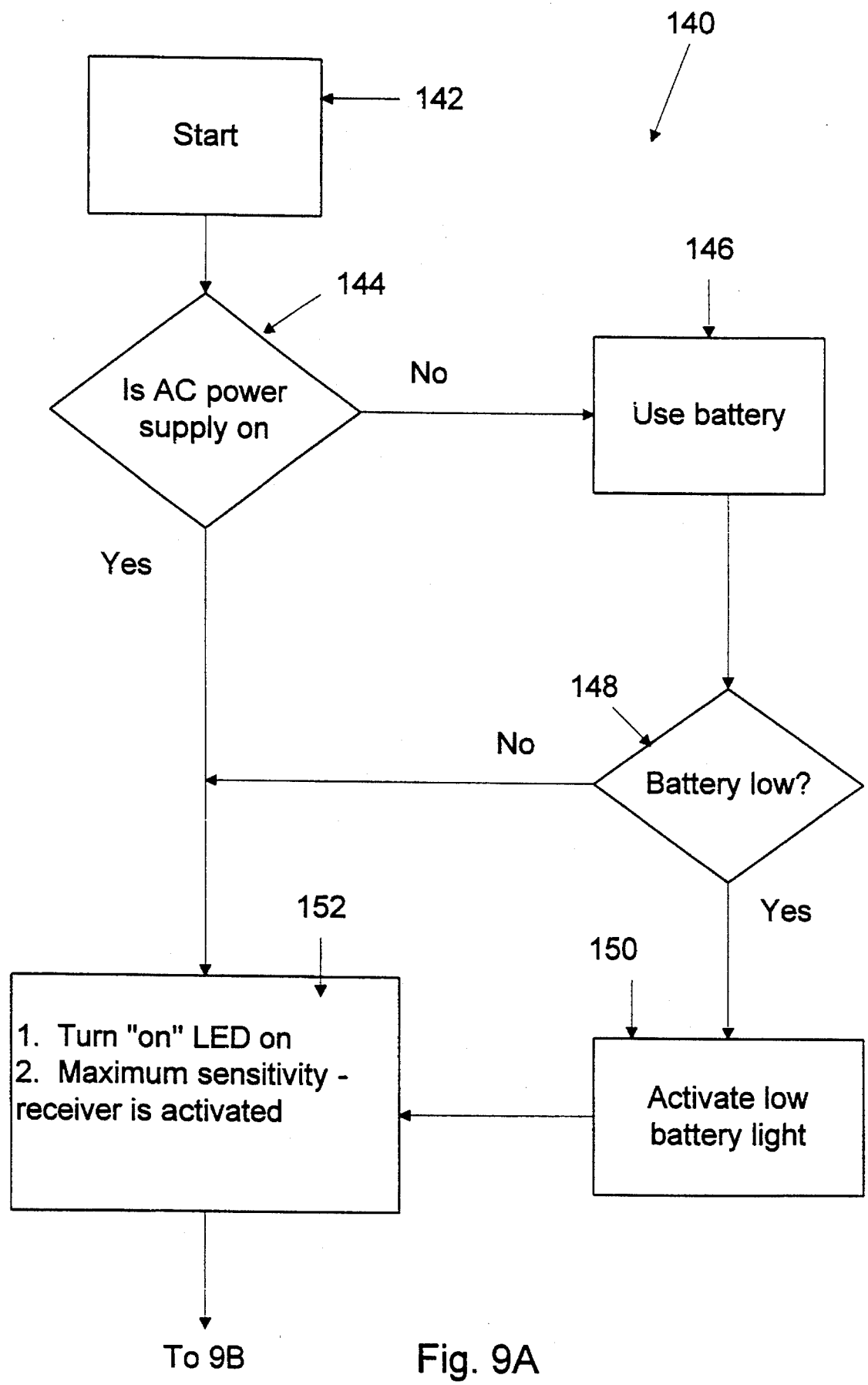
FIG. 9 is a flow chart of the operation of the internal circuitry of the controller of FIGS. 5 and 6.
Figure 9B:
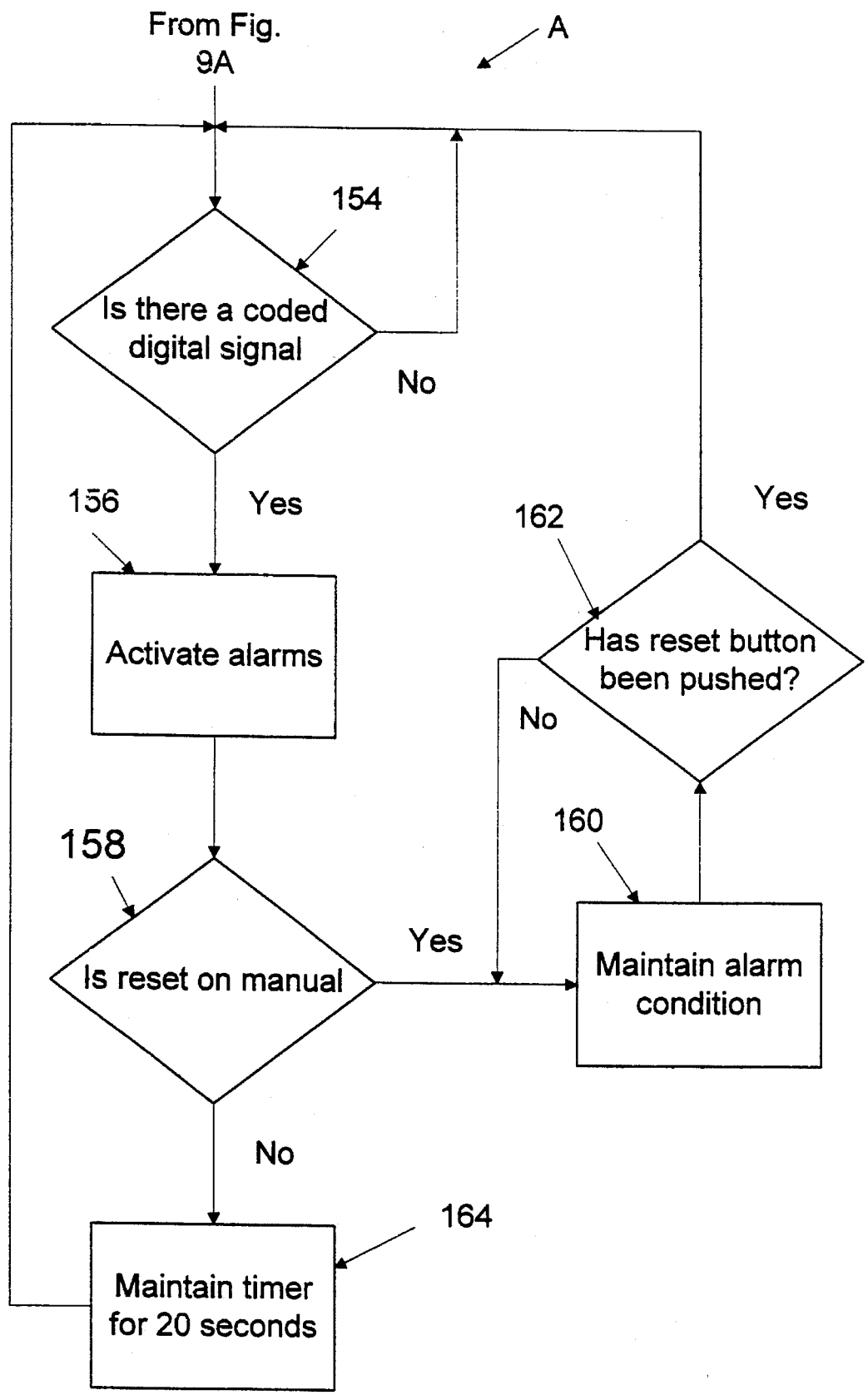

Referring now particularly to FIGS. 7–9, the bed monitoring system 20 operates as follows.

First, the primary antenna 24 is placed beneath the mattress or mattress pad of the bed 22 or in another suitable location, and the control module 38 is placed on a stand on the floor near the bed 22 and plugged into the primary antenna 24 and to the external power source 64, and the controller 32 is placed in a remote room 42 occupied by the caregiver and is then connected to power source 96. A routine 100 defined by the circuitry within the control module 38 then proceeds from start at step 102 in FIG. 8 to determine in step 104 whether or not the external power source 64 is active. If not, the battery backup is activated in step 106, and the routine then confirms that the power is on in step 108. The routine 100 then proceeds to step 110 where the control module 38 supplies energizing current to the primary antenna 24 at a level selected by operation of height adjust dial 74. The LED pilot light 72 is also illuminated at this time to apprise the caregiver that the control module 38 is operational.

The bracelet module 26, having been previously strapped to the monitored person's ankle with the ankle bracelet 44, operates as follows with reference to FIG. 7. The routine 120 defined by the circuitry within bracelet module 26 proceeds from start at step 122 to step 124, where it initiates a relatively short timing function (a few milliseconds in the illustrated embodiment) which determines the intervals at which the remainder of the routine is executed. The routine 120 then proceeds to step 126 in which the primary antenna signal strength as detected by the first or bracelet receiver 28 is compared to a threshold, thereby detecting whether or not the bracelet module 26 is in the designated volume 25. If so, no further action need be taken, and the routine 120 returns to start at step 122. If not, the routine 120 determines that the bracelet module 26 is outside of the designated volume 25 and proceeds to step 128 where a signal is transmitted by the bracelet transmitter 30 for a short burst of, e.g., 3 milliseconds. An 11 second timing circuit is also started at this time. Next, the routine 120 proceeds to step 130 where it is determined whether or not a primary antenna field of sufficient strength is again detected by receiver 28 after the short burst. If not, the routine 120 proceeds to step 132 where it is determined whether or not the reset 11 second period has expired. If not, generation of another signal pulse is delayed until the antenna field above the threshold strength is either present or until the 11 second period has expired. If, on the other hand, it is determined in step 130 that an antenna field of sufficient strength is again present, the routine 120 determines that the bracelet module 26 is back inside the designated volume 25, the bracelet transmitter 30 is deactivated in step 134, and the routine 120 returns to start at step 122.

Thus, the bracelet transmitter 30 transmits a signal whenever the bracelet module 26 leaves the designated volume 25 and repeats this transmission in 11 second increments only for as long as the bracelet module 26 remains outside of the designated volume 25. Because an alarm signal will be generated whenever the bracelet transmitter 30 is activated, an alarm will be sounded whenever the monitored person's foot or another monitored part of the anatomy leaves the volume 25, thus permitting an alarm signal to be generated before the person's feet ever touch the floor. This permits the caregiver to reach the monitored person and to prevent him or her from leaving the bed 22 before he or she falls or wanders away from the bed. Nuisance signals are also reduced by ceasing transmission whenever the bracelet module 26 re-enters the volume 25 (assuming that the system 20 is in the auto reset mode). As discussed above, nuisance alarms am further reduced through the use of the three dimensional antenna array for bracelet receiver 28 which virtually assures that the presence of the bracelet module 26 in the volume 25 will always be detected. This negates the need for the caregiver to run to the user's side whenever he or she tosses or turns or only temporarily leaves the designated volume 25. It should also be noted that the system 20 has an inherent safety feature such that, in the event of hilum of the primary antenna 24 or its power source (control module 38), the disabling signal generated thereby will automatically cease, resulting in generation of an alarm signal.

Referring now to FIG. 9, the controller 32 receives the signal from the bracelet transmitter 30 and generates an alarm in the following manner. First, the controller routine 140 proceeds from start at step 142 to determine in step 144 whether or not the AC power supply 96 is on. If not, the battery backup is activated in step 146, and it is then determined in step 148 whether or not the battery is low. If so, the LOW BATTERY LED 86 is illuminated in step 150. In either event, or if the AC power supply 96 is on, the routine 140 proceeds to step 152 in which the POWER ON LED 84 is illuminated and the second receiver or antenna 34 is activated. The routine 140 then proceeds to step 154 in which it is determined whether or not a coded signal is being transmitted by the bracelet transmitter 30. If not, no alarm need be generated, and the routine 140 returns to step 154. If so, the alarm(s) is/are activated in step 156. The routine 140 then proceeds to step 158 in which it is determined whether or not the manual reset mode has been activated by dial 88. If so, the alarm condition is maintained by operation of step 160 until it is determined in step 162 that the manual reset button 82 has been pushed, at which time the routine 140 returns to step 154. If not, a timer is triggered in step 164 to automatically maintain the alarm for 20 seconds before returning to step 154. Thus, the controller 32 is operable in conjunction with the bracelet module 26 to generate an alarm signal for 20 seconds or until manually reset each time the coded three millisecond burst is received from the bracelet transmitter 30. This assures a continuous alarm until the controller 32 is reset or bracelet signal reception ceases. Should the condition leading to the generation of the alarm signal cease, the alarm signal will not be regenerated upon reset, and the caregiver will be apprised that there is no need to check on the monitored person.

B. Healthcare Institution Bed Monitoring System

Referring now to FIGS. 10–13, a bed monitoring system 220 is illustrated which is conceptually the same as that illustrated in FIGS. 1–9 but which is designed for use in nursing homes, hospitals, or other healthcare institutions. System 220 differs operationally from the system 20 described in Section 2A primarily in that its bracelet transmitter emits a shorter range but essentially continuous signal and in that the alarm signal is additionally transmitted to a remote location such as a nurse's station. Elements of the system 220 of FIGS. 10–13, being conceptually similar to those of system 20 of FIGS. 1–9, is thus designated by the same reference numerals, incremented by 200.

Monitoring system 220 includes a primary antenna 224; a bracelet module 226 mounted on a bracelet (not shown); and a controller 232 which combines the functions of the control module and controller of the first embodiment and which is thus located in proximity to and connected directly to the primary antenna 224. Although controller 232 is illustrated in use with a single primary antenna 224 and bracelet module 226, multiple antennas and bracelet modules could be associated with each controller such that a single controller could be used to monitor a semi-private room or even an entire ward.

Controller 232 includes a casing 276 having the second receiver or antenna 234 and a visual alarm indicator 278 located on an upper surface thereof and having an alarm generator 236 disposed therein. Located on the front face of the casing 276 is a power switch 280, manual reset switch 282, POWER ON and LOW BATTERY LED indicators 284 and 286, and a field height control dial 274 operationally identical to the field height control dial 74 of the first embodiment. Located on the rear face of the casing 276 are reset mode and audible alarm select dials 288 and 290 identical to those of the first embodiment, a power jack 292 connecting the controller 232 to an external AC power source 296 via a cord 298, and an output jack 268 supplying power to the primary antenna 224 via a cord 246. A second output jack 293 receives a cord 299 which can be plugged into a nurse's call station 297 to transmit an alarm signal thereto. Located within the casing 276, in addition to control circuits performing the control module and controller functions detailed above, is a 40-day rechargeable backup battery (not shown) capable of supplying power to both the controller 232 and the primary antenna 224.

Figure 10:
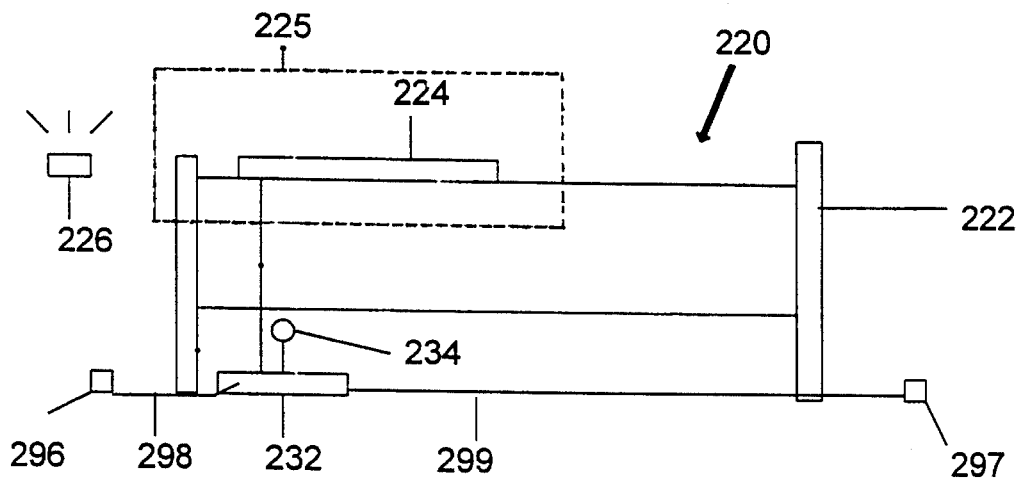
FIG. 10 schematically represents a bed monitoring system constructed in accordance with a second embodiment of the invention and designed primarily for use by healthcare institutions.
Figure 14:
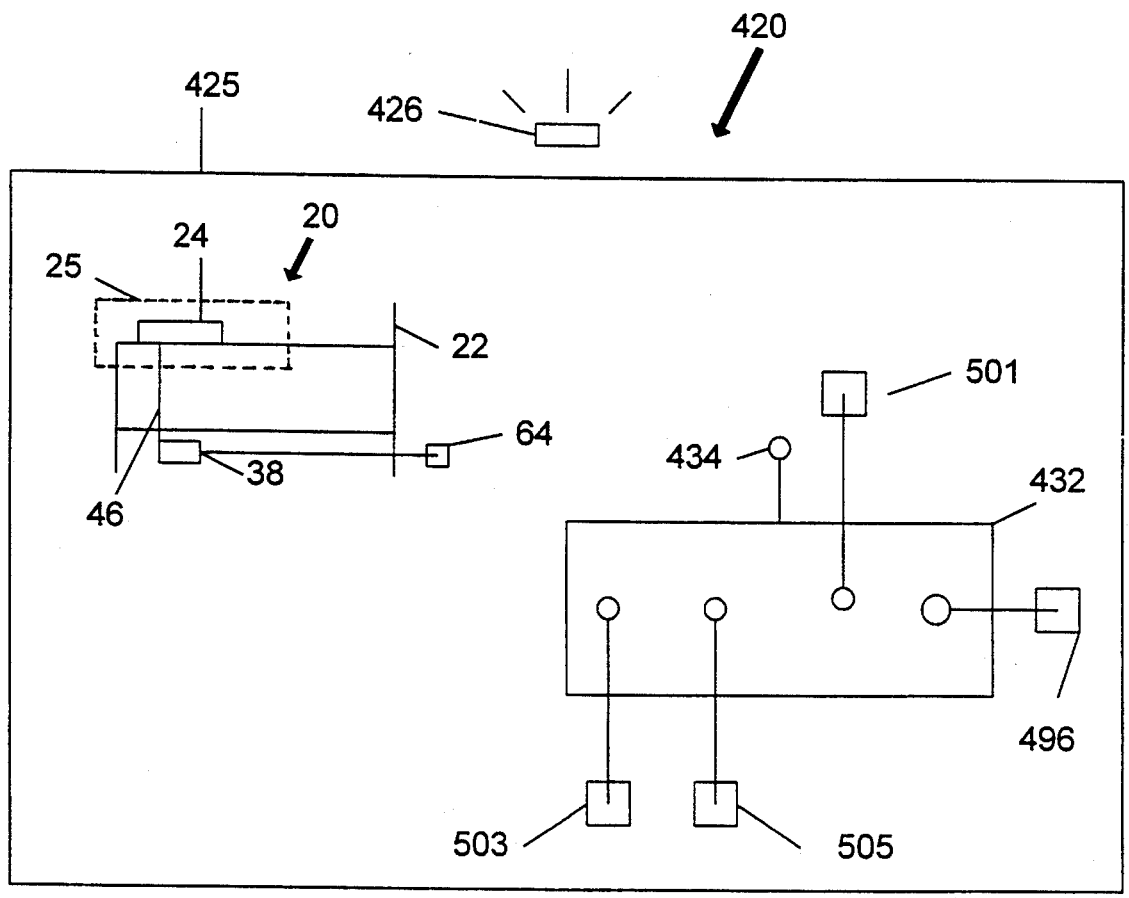
FIG. 14 schematically illustrates a monitoring system constructed in accordance with a third embodiment of the invention usable as both an home/area monitoring system and a bed monitoring system.
Figure 11:
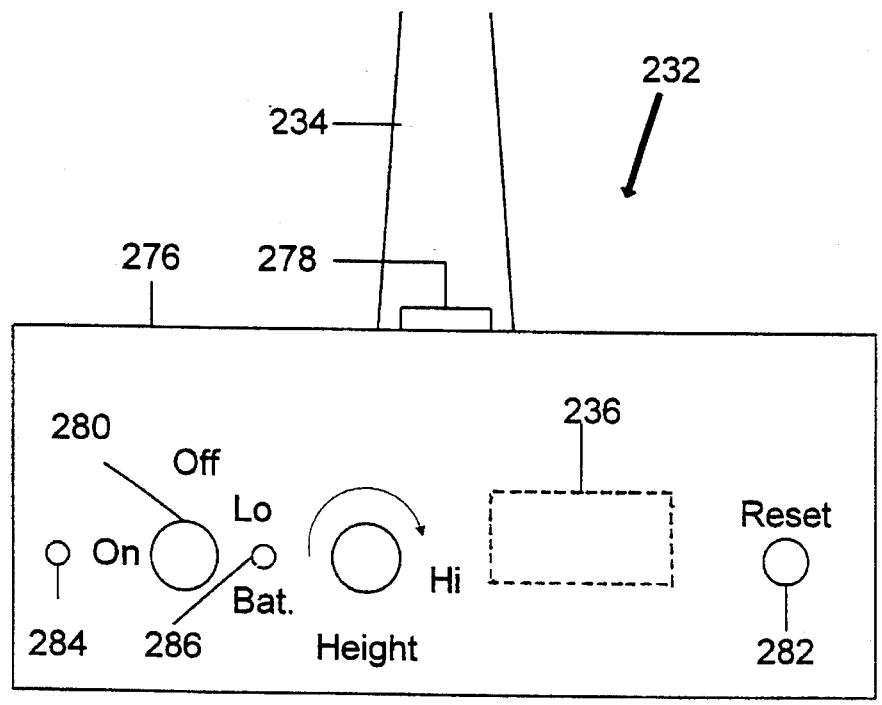
FIG. 11 is a partially schematic front elevation view of the controller of the system of FIG. 10.
Figure 12:
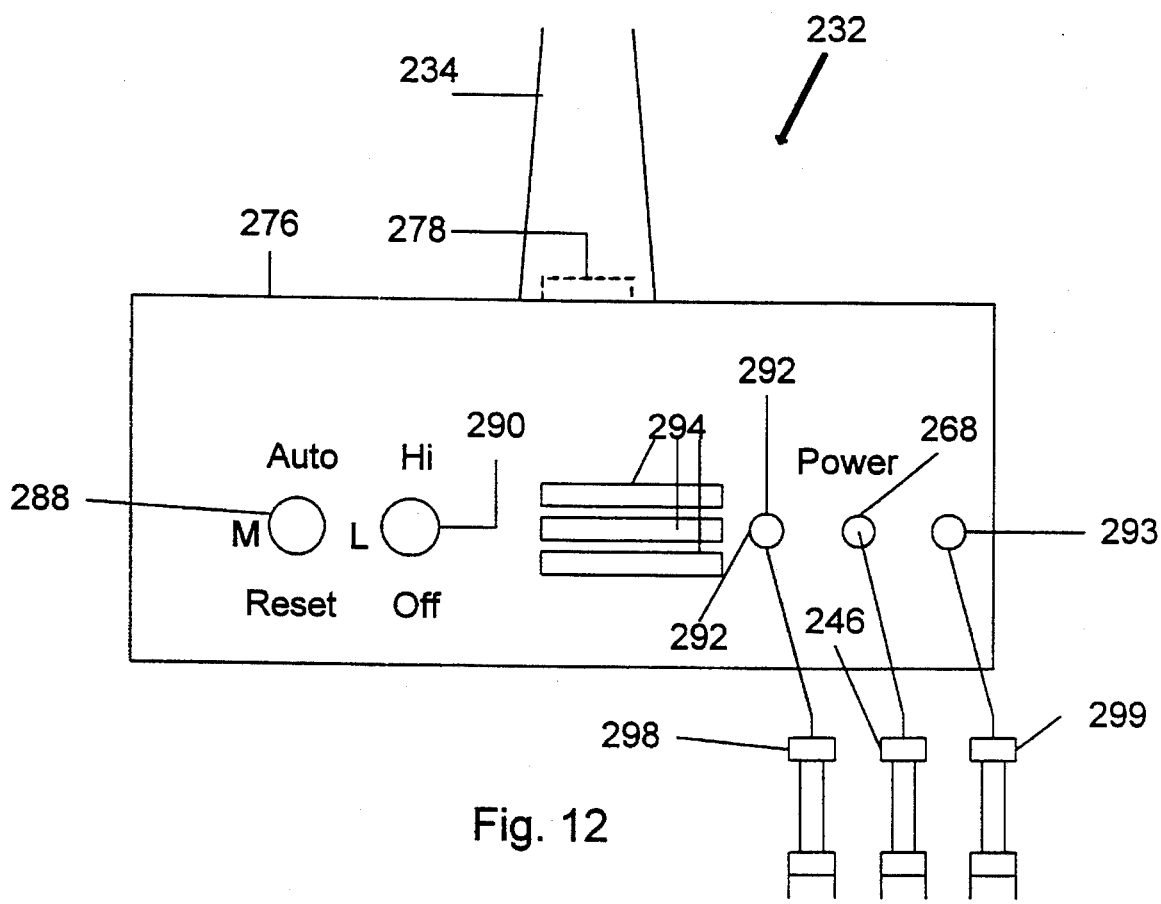
FIG. 12 is a partially schematic rear elevation view of the controller of FIG. 11.
Figure 13:
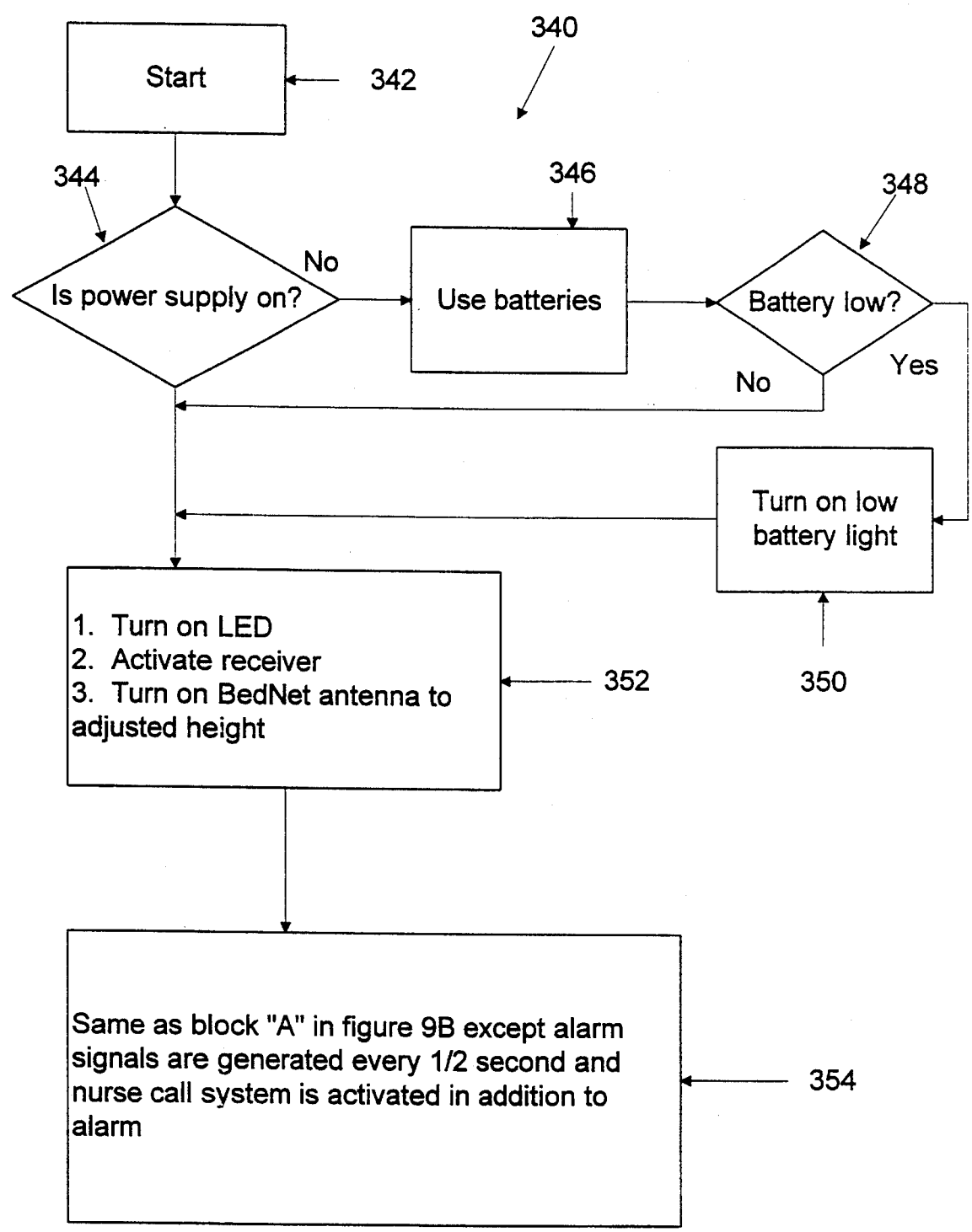
FIG. 13 is a flow chart of the functions performed by the internal circuitry of the controller of FIGS. 11 and 12.
Figure 15:
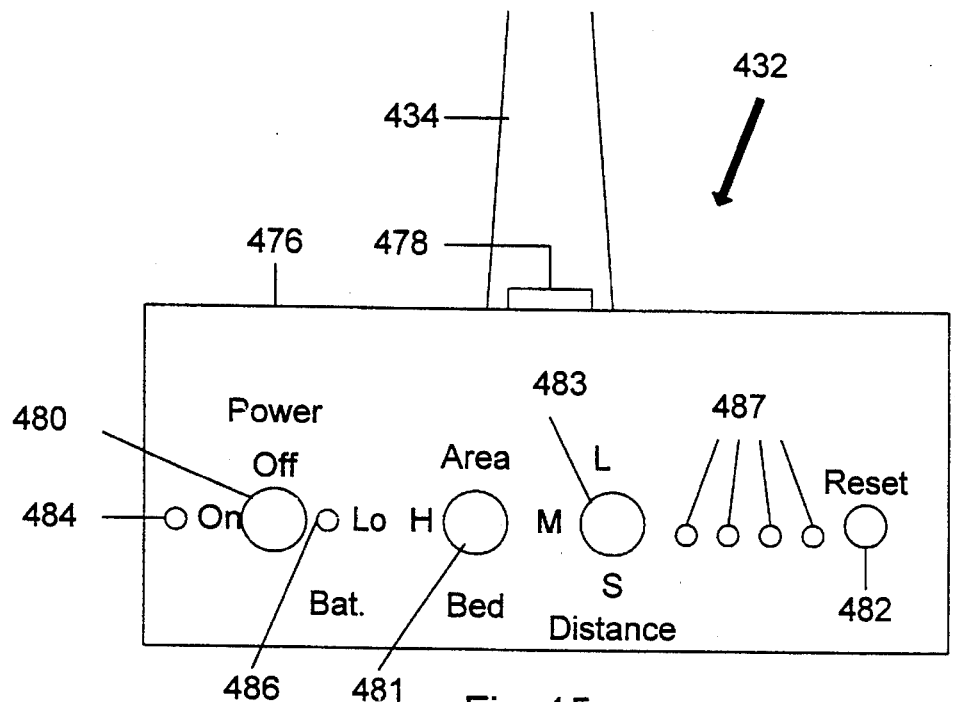
FIG. 15 is a partially schematic front elevation view of the controller of the system of FIG. 14.
Figure 16:
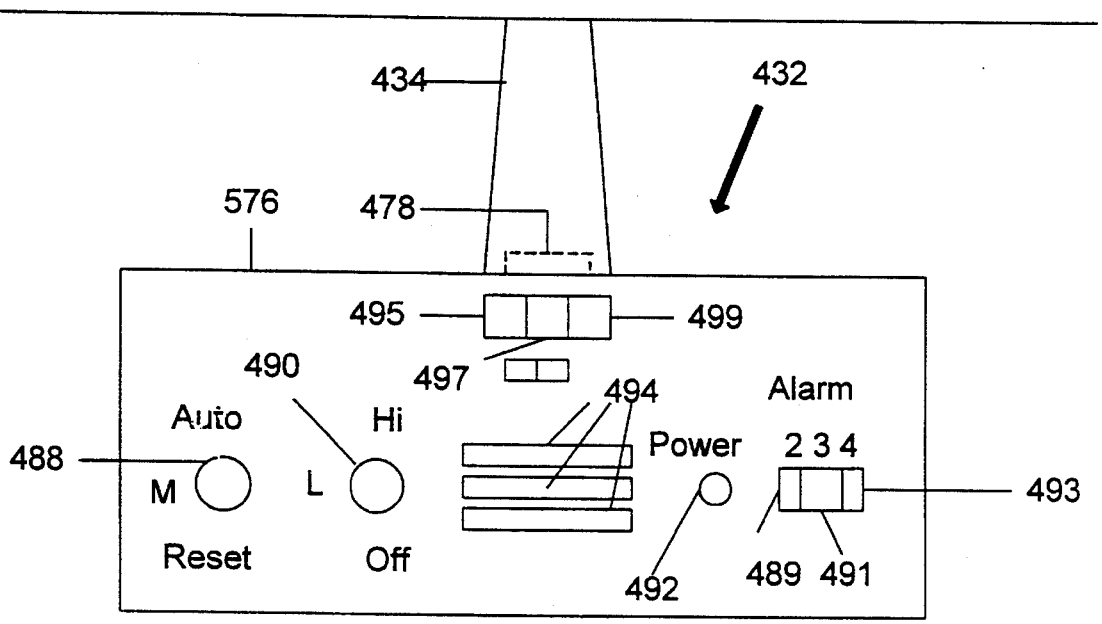
FIG. 16 is a partially schematic rear elevation view of the controller of FIG. 15.

The operation of the monitoring system 220 of FIGS. 10–12 is similar to that of FIGS. 1–9 with the functions of the controller and control module being combined in a single controller 232. Thus, referring to FIG. 13, the internal controller routine 340 proceeds from start at step 342 and determines whether or not the AC power supply 296 is on in step 344. If not, the backup batteries are activated in step 346, and it is determined in step 348 whether or not battery strength is above a threshold. If not, the LOW BATTERY LED 286 is illuminated in step 350. In any event, the routine 340 proceeds to step 352 in which the POWER ON LED 284 is illuminated, the second receiver or antenna 234 is activated, and power is supplied to the primary antenna 224 to produce a signal field volume 225 the height of which is selected by adjustment of the dial 274. Monitoring then proceeds as discussed in section 2A above with the exception that the bracelet signal is transmitted at a lower power (having a range of above ⅓ to ½ that of transmitter 30) so as to avoid interference between adjacent systems, but is generated in a train of pulses spaced ½ second apart to assure receipt by the second receiver 234. In addition, the alarm signal is transmitted to the nurses call station 297 via jack 293 and cord 299 in addition to the visual and/or audible alarms.

It should be noted that while both of the embodiments discussed above are described for use with a bed and an ankle bracelet, they could be modified to meet the needs of a particular application. For instance, if a person's wrist needed to be immobilized for any reason, a smaller primary antenna could be used near the head of a bed or on a chair or the like to monitor the wrist location.

3. Home/Area Monitoring System

The bed monitoring systems 20 and 220 described above are ideally suited for monitoring persons who are relatively immobile or who are mobile but may wander away from bed. However, it is often desired to monitor the activities of persons who are mobile and who may wander during the daylight hours, and such monitoring can be performed by the home/area monitoring system 420 illustrated in FIGS. 14–17B. This system 420 takes advantage of the fact that the strength of the signal received by the second receiver in the controller decreases with increased distance from the bracelet transmitter to the controller. The system 420 thus includes the bracelet 44 and associated module 26 (including the receiver 28 and transmitter 30 in FIG. 3), and a controller 432. The system 420 is also preferably capable of operating as a bed monitoring system of the type described in Section 2A above and thus also includes a primary antenna 24 mountable on a bed 22 or the like and a control module 38 connected to the primary antenna 24 and to a power source 64. The bracelet module 26, primary antenna 24, and control module 38 are identical to those discussed in section 2A above, are denoted by reference numerals corresponding to those of the corresponding elements, and are not discussed in greater detail.

The controller 432 incorporates all of the features of the controller 32 of the first embodiment and thus includes a power switch 480, a manual reset switch 482, a POWER ON LED indicator 484, a LOW BATTERY LED indicator 486, reset mode and audible alarm select dials 488 and 490, a power jack 492, and vents 494, all mounted on a casing 476. Controller 432 also includes features for switching between various operational modes and for programming various alarm modes. To this end, a dial 481 is provided permitting the selection between a "BED" monitoring mode, a "HOME" monitoring mode, and an "AREA" monitoring mode. A range dial 483 is provided to vary the detection distance between short, medium, and long in each of the "HOME" and "AREA" monitoring modes. Alarm indicator LEDs 487 are further provided on the front face of the casing 476, and alarm switches 489, 491, and 493 and remote output jacks 495, 497, and 499 are provided on the rear face of the casing 476. The rear output jacks 495, 497, and 499 are connected to a remote operated reset device 501, a remote alarm 503, and an autodialer 505, respectively. Autodialer 505 automatically dials a remote cellular telephone a designated period of, e.g., 60 seconds after an autodialer timer, preferably incorporated into the electronics of controller 432, is activated. Preferably, this timer cooperates with the remaining controller electronics such that the timer is disabled if reset occurs of if bracelet signal transmission resumes during a designated delay period.

While many of the features described above should be self-explanatory, further comments are believed to be in order with respect to other features. The mode select dial 481 controls the internal circuitry of the controller 432 to vary the sensitivity and/or frequency range of the system 420. Specifically, when the mode select dial 481 is set in the "BED" mode, the relatively short range 150 khz signal from the primary antenna 24 is continuously monitored by the bracelet receiver 28, and the bracelet transmitter 30 transmits 315 khz signals to the controller 432 only under alarm conditions. On the other hand, the relatively long range 315 khz is continuously transmitted by the bracelet transmitter 30 and monitored by the controller 432 whenever the mode select dial 481 is turned to the "HOME" or "AREA" setting, and an alarm signal is generated whenever this bracelet signal drops below a designated strength. Sensitivity within either the "HOME" or "AREA" modes can be adjusted through operation of the range select dial 483 which varies the range from the controller 432 movement beyond which will result in the generation of an alarm signal, thereby designating a "safe" area 425 in FIG. 14. The mode select dial 481 is thus capable of first switching the system 420 between basic operational states, i.e., from bed monitoring to home or area monitoring and, when the system 420 is in the home/area operational state, is capable of selecting one of a multiple, in this case two, strength ranges. The range select dial 483 is capable of selecting a designated strength within a range selected by the mode select dial 481. The selection of monitored distances, and thus the size of the "safe" area 425, using these two dials can be exemplified by the following table:

| Mode/Distance Setting | Approximate Distance |
| --- | --- |
| Home/short | 15–25 feet |
| Home/medium | 25–30 feet |
| Home/long | 50–60 feet |
| Area/short | 75–90 feet |
| Area/medium | 125–140 feet |
| Area/long | 175–200 feet |

The monitoring system 420 operates as follows.

Figure 17A:
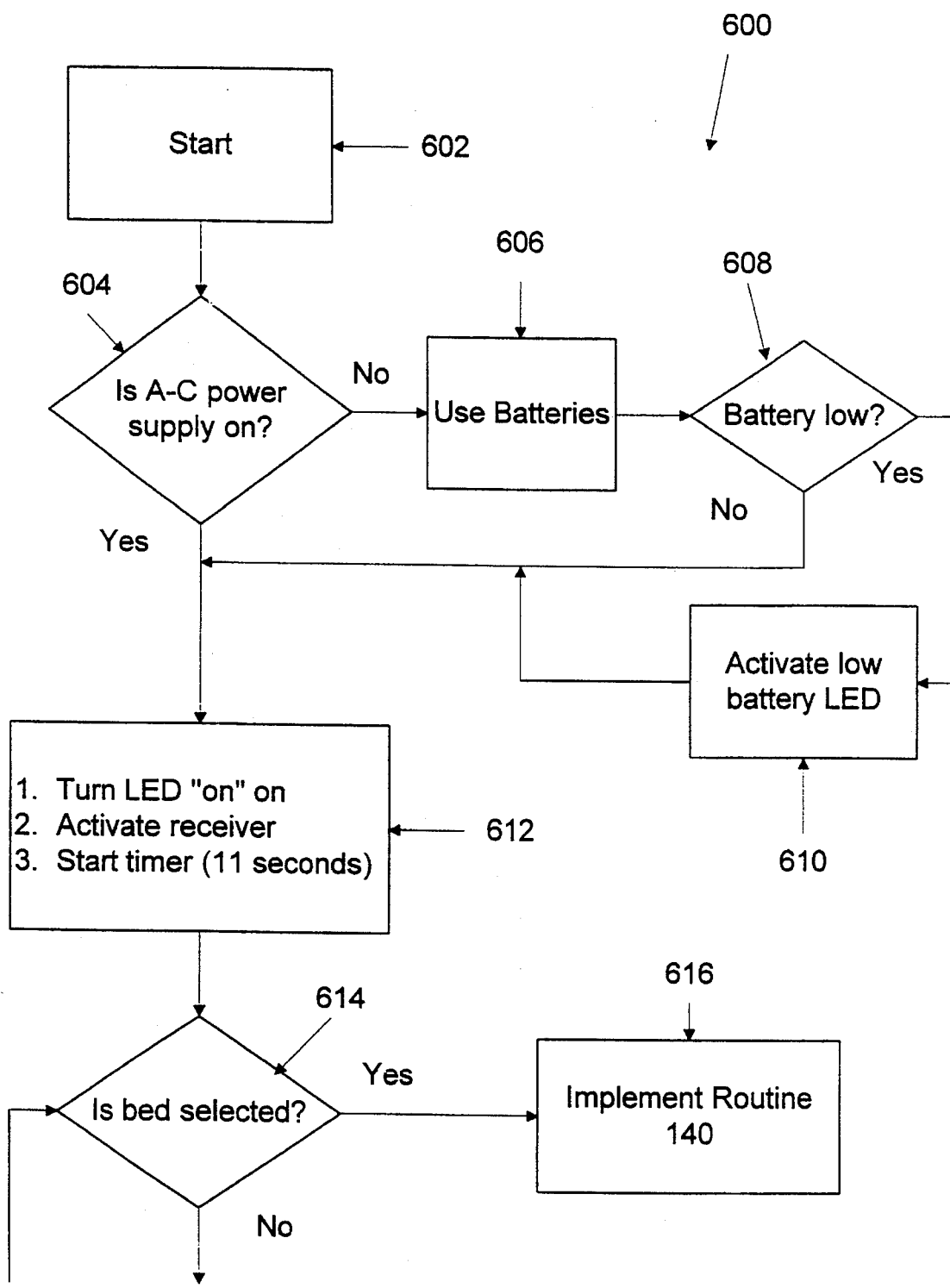
FIG. 17A, 17B and 17C collectively comprise a flow chart of the operation of the internal circuitry of the controller of FIGS. 15 and 16.
Figure 17B:
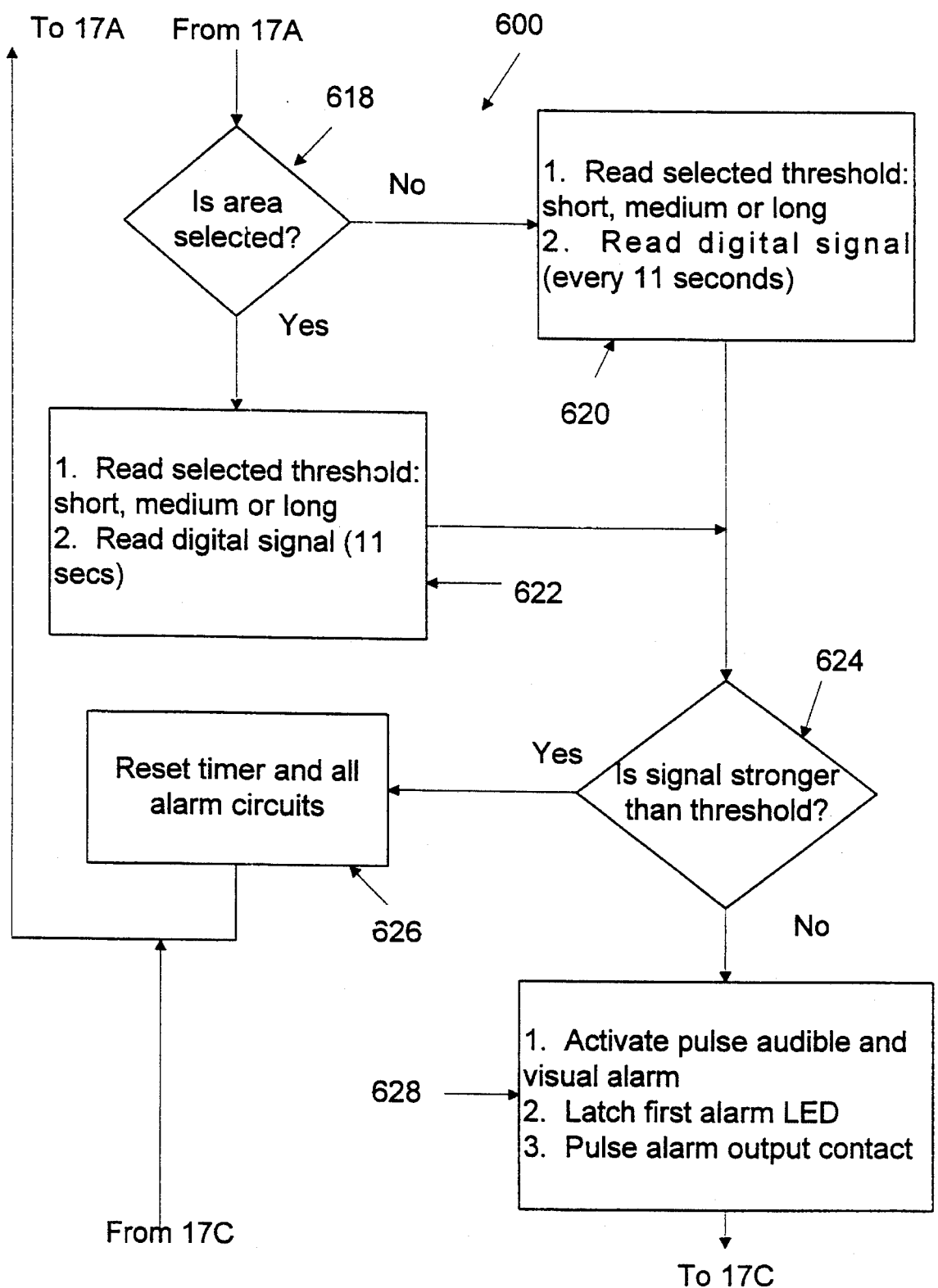
Figure 17C:
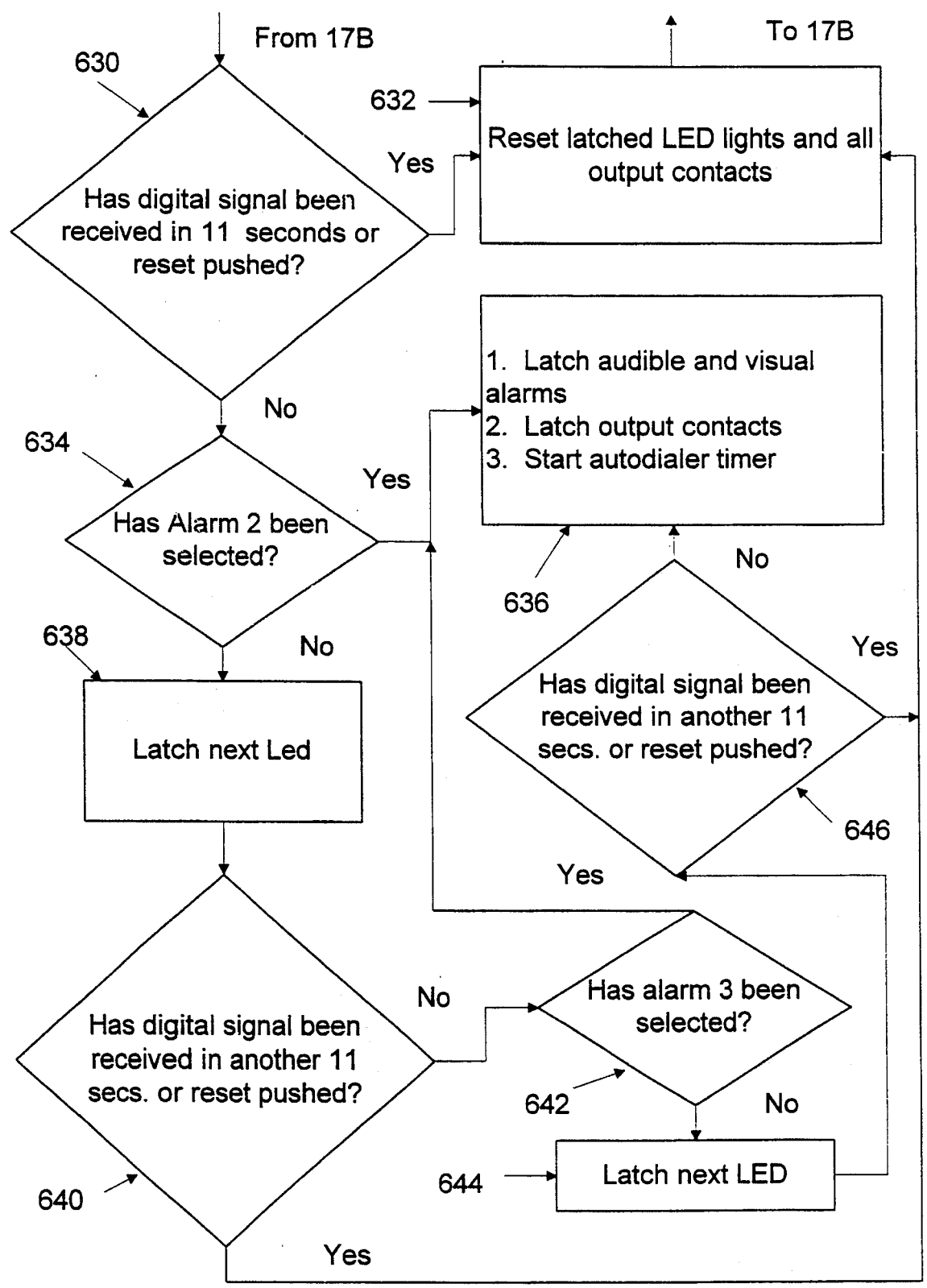

The routine 600 defined by the internal circuitry of controller 432 proceeds from start at step 602 in FIG. 17A to step 604 where it determines whether or not the AC power supply 496 is on. If not, the batteries are activated and tested and signals generated in steps 606, 608, and 610 in the same manner as discussed in Sections 2A and 2B above. In any event, the routine 600 proceeds to step 612 where the POWER ON LED 484, the second receiver 434, and the internal 11 second timer in the controller 432 are all activated. The routine 600 then proceeds to step 614 and determines whether or not the BED monitoring mode has been selected by dial 481 and, if so, the routine 140 of FIG. 9 is implemented in step 616. If not, the routine 600 proceeds to step 618 where it is determined whether or not the "AREA" monitoring mode is selected. If not, it is assumed that the "HOME" mode has been selected, and the threshold selected by range select dial 483 is read in step 620 and combined with the setting of mode select dial 481 to set a signal strength threshold corresponding to the selected "safe" area 425. If, on the other hand, the answer to the inquiry in step 618 is YES, a second threshold is selected in step 622 using the same distance setting and the other area setting. In either event, the routine 600 proceeds to step 624 where it is determined whether or not the signal received from the bracelet transmitter 30 is stronger than the selected threshold. If so, the routine determines that the monitored person is within the "safe" area 425, the timer and all alarms are reset in step 626, and the routine returns to step 614. If the answer to the inquiry of step 624 is NO, indicating that the monitored person has either left the "safe" area 425 or the bracelet transmitter 30 is not transmitting or its signal is blocked, the routine 600 proceeds to step 628 where the first alarm LED 487 is illuminated, visual alarm 478 and external alarm are briefly activated, and an audible alarm on the controller 432 may depending upon the setting of dial 490 be briefly activated.

However, more continuous operation of the external alarm 503 and triggering of the autodialer 505 may, depending upon the setting of alarm switches 489, 491, and 493, not be activated at this time. Rather, the caregiver may want to minimize nuisance alarms and to give the monitored person time to return to the "safe" area by preventing continuous activation of external alarm(s) 503 and/or activation of the autodialer 505 unless the signal from the bracelet transmitter 30 drops below the selected threshold for at least one and possibly several multiples of a designated period of time such as 11 seconds. Thus, the routine 600 proceeds to step 630 where it is determined whether or not a signal above the designated threshold has been received within an 11 second period. If so, the routine 600 proceeds to step 632 where the previous alarm signal is treated as false or corrected, the audible and visual alarms are deactivated, and the accompanying LEDs are unlatched, and the routine 600 then returns to step 602. If the answer to the inquiry of step 630 is YES, thus indicating that the alarm signal has been maintained for 11 seconds without a manual reset, the routine 600 proceeds to step 634 where it is determined whether or not the second alarm mode has been selected by actuation of switch 489. If so, the routine 600 proceeds to step 636, where the audible and visual alarms remain latched, the contacts for the external alarm 503 are latched, and the internal timer for autodialer 505 is started. If the answer to the inquiry of step 634 is NO, the next LED 487 is latched in step 638 before determining in step 640 whether or not a digital signal from bracelet transmitter 30 or a reset command has been received in an additional 11 second period, and then the routine 600 proceeds to either step 642 or returns to step 636, depending upon the result. Similar inquiries are made in steps 642 and 646 and, in each case, the final LED indicator 644 is latched (if necessary) and the alarm(s) 503 is latched and the autodialer timer is activated if the additional period has expired without receiving a signal from the bracelet transmitter 30, and the routine 600 proceeds to step 636 unless the signal from the bracelet transmitter 30 is received in the additional period. Alarm signal generation can be terminated at any time during this procedure either by actuation of manual reset switch 482 or by receipt of a remote reset signal from a device 501 which may comprises a telephone or radio transmitter. Nuisance signals can thus be sharply reduced by delaying the generation of relatively strident alarm signals for device 505 until the absence of a signal of sufficient strength from bracelet transmitter 30 is detected for a designated adjustable period.

It can thus be seen that in addition to providing alarm displays on the controller 432, the system 420 is capable of generating alarms at remote locations or even autodialing a cellular telephone or the like and is also capable of being reset from a remote location. It should be noted that while these particular functions have been described solely in connection with the third embodiment, some or all could also be incorporated into the first and second embodiments. The system could also be used in conjunction with existing tracking systems. Many other changes could be made to the invention without departing from the spirit thereof. For instance, the distances and periods described above are given solely by way of example and could be varied widely depending upon a particular application. The specific construction and function of each embodiment could also be varied significantly while still adhering to the basic inventive concept. The scope of these and other changes will become more apparent from the appended claims.

I claim:

1. A monitoring system comprising:
   (A) a first transmitter which generates a first, RF signal forming a signal field a portion of which is above a designated strength and encompasses a designated spatial volume in which at least a designated anatomical part of a non-ambulatory monitored person is positionable for monitoring;
   (B) a module which is worn on said designated anatomical pan of said monitored person and which includes
      (1) a first receiver capable of receiving said first signals, and
      (2) a second transmitter which is coupled to said first receiver and which transmits a second signal except when the first signal as received by said first receiver is above said designated strength;
   (C) a second receiver which detects the presence or absence of said second signal, thereby detecting whether or not said designated anatomical pan of said monitored person is located within said designated spatial volume; and
   (D) an alarm generator which is coupled to said second receiver and which generates an alarm signal when said second receiver receives said second signal.

2. A system as defined in claim 1, wherein said first transmitter comprises a generally planar primary antenna formed from a plurality of interconnected wire loops mounted on a flat sheet.

3. A system as defined in claim 2, further comprising an adjustable power source connected to said primary antenna and operable to vary the designated spatial volume by varying the power supplied to said primary antenna, thereby varying the source strength of said first signal.

4. A system as defined in claim 3, further comprising (1) a control module in which is mounted said power source and (2) a controller which is located remote from said controller and in which is mounted said second receiver and said alarm generator.

5. A system as defined in claim 4, wherein said second transmitter transmits said second signal immediately when said first receiver leaves said designated spatial volume after being located within said designated spatial volume and then transmits said second signal at intervals of greater than 10 seconds.

6. A system as defined in claim 3, wherein said power source, said second receiver, and said alarm generator are combined in a single controller.

7. A system as defined in claim 6, wherein said second transmitter transmits said second signal immediately when said first receiver leaves said designated spatial volume after being located within said designated spatial volume and then transmits said second signal at less than 1 second intervals.

8. A system as defined in claim 6, further comprising a nurse's call station and means, located in said controller, for transmitting said alarm signal to said nurse's call station.

9. A system as defined in claim 1, further comprising means, connected to said first receiver and said first transmitter, for disabling operation of said second transmitter unless first signals as received by said first receiver is above said designated strength and for otherwise triggering operation of said second transmitter.

10. A system as defined in claim 1, wherein said first receiver comprises an array of three receiving antennas, each of which is attuned to a different directional axis.

11. A system as defined in claim 1, further comprising means for switching said system from a first operational state in which said alarm generator generates said alarm signal whenever said second receiver receives said second signal to a second operational state in which said alarm generator generates said alarm signal only when said second signal as received by said second receiver drops below a threshold strength.

12. A system as defined in claim 11, wherein said first transmitter and said first receiver operate on a first frequency and said second transmitter and said second receiver operate on a second frequency which is higher than said first frequency, and wherein said first receiver continuously monitors signals of said first frequency when said system is in its first operational state and said second receiver continuously monitors signals of said second frequency when said system is in its second operational state.

13. A system as defined in claim 11, further comprising means for transmitting said alarm signal to a remote device selected from the group consisting of an alarm and an autodialer.

14. A system as defined in claim 11, further comprising means, operable when said system is in said second operational state, for (1) selecting one of multiple designated ranges of said threshold strength for said second signal and for (2) adjusting said threshold strength within the selected range of threshold strengths.

15. A monitoring system comprising:
(A) a generally planar RF antenna which is formed from a plurality of interconnected wire loops mounted on a flat sheet and which generates a first, RF signal forming a signal field a portion of which is above a designated strength and encompasses a designated spatial volume in which at least a designated anatomical part of a non-ambulatory monitored person is positionable for monitoring;
(B) a bracelet which is worn by said monitored person;
(C) a first receiver mounted on said bracelet, said first receiver including an array of three receiving antennas, each of which is attuned to a different directional axis and is capable of receiving said first signal;
(D) a second transmitter which is mounted on said bracelet, which is coupled to said first receiver, and which transmits a second signal except when the first signal as received by said first receiver is above said designated strength;
(E) an adjustable signal generator which is connected to said RF antenna and which selectively causes said RF antenna to vary the designated spatial volume;
(F) a second receiver which is located remote from said bracelet and which detects the presence or absence of said second signal, thereby detecting whether or not said designated anatomical part of said monitored person is located within said designated spatial volume; and
(G) an alarm generator which is coupled to said second receiver and which generates an alarm signal whenever said second receiver receives said second signal.

16. A system comprising:
(A) transmitter/receiver means, worn on a designated anatomical part of a user, for automatically ascertaining whether or not said designated anatomical pan of said user is located within a monitored spatial volume in which said designated anatomical part of said user is located when said user is non-ambulatory and for automatically transmitting a signal only when said designated anatomical part of said user is located outside of said monitored spatial volume;
(B) means for receiving said signal from said transmitter/receiver means and for generating an alarm signal only when said designated anatomical part of said user is located outside d said designated spacial volume; and
(C) means, responsive to said means for receiving, for displaying an alarm.

17. A method comprising:
(A) detecting whether or not a receiver, mounted in a device worn on a designated anatomical part of a monitored person, is located in a designated spatial volume in which said designated anatomical part of said monitored person is located when said monitored person is non-ambulatory;
(B) automatically transmitting a signal from said user worn device, in response to said detecting step, only when said receiver and said designated anatomical part of said monitored person are located outside of said designated spatial volume; and
(C) generating an alarm signal only in the presence of said signal from said user worn device.

18. A method as defined in claim 17, further comprising varying the designated spatial volume.

19. A method as defined in claim 17, further comprising transmitting said alarm signal to a remote device.

20. A method as defined in claim 19, wherein said step of transmitting said alarm signal comprises transmitting said alarm signal to a nurse's call station.

21. A monitoring system comprising:
(A) a transmitting antenna which transmits a first signal forming a signal field a portion of which is above a designated strength and encompassing a designated spatial volume in which at least a designated anatomical part of a non-ambulatory monitored person is positionable for monitoring;
(B) a first receiver which is worn by said monitored person and which receives said first signal;
(C) a transmitter which is worn by said monitored person and which transmits a second signal, said transmitter transmitting said second signal except when said first signal as received by said first receiver is above said designated strength;
(D) a second receiver which is located remote from said first receiver and said transmitter and which receives said second signal, thereby detecting whether or not said designated anatomical pan of said person is located within said designated spatial volume; and
(E) a controller including
  (1) an alarm generator which is coupled to said second receiver and to said threshold setting means, and
  (2) means, coupled to said alarm generator, for switching said system from a first operational state in which said alarm generator generates an alarm signal whenever said second receiver receives said second signal to a second operational state in which said alarm generator generates said alarm signal only when the strength of said second signal as received by said second receiver drops below a threshold strength.

22. A monitoring system as defined by claim 21, further comprising threshold setting means, coupled to said second receiver, for setting said threshold strength, said threshold setting means comprising means for (1) selecting one of multiple designated ranges of said threshold strength and for (2) adjusting said threshold strength within the selected range of threshold strengths.

23. A monitoring system comprising:
(A) a bed;
(B) a generally planar RF antenna which is supported on said bed and which is formed from a plurality of interconnected wire loops mounted on a flat sheet, wherein said RF antenna generates a first, RF signal forming a signal field above said bed, a portion of said signal field being above a designated strength and encompasses a designated spatial volume in which at least a designated anatomical part of h non-ambulatory monitored person is positionable for monitoring;

(C) a bracelet which is worn on said designed anatomical part of said monitored person;

(D) a first receiver mounted on said bracelet, said tint receiver including an array of three receiving antennas, each of which is attuned to a different directional axis and is capable of receiving said first signal;

(E) a second transmitter which is mounted on said bracelet, which is coupled to said first receiver, and which transmits a second signal except when the first signal as received by said first receiver is above said designated strength;

(F) an adjustable signal generator which is located adjacent said bed, which is connected to said RF antenna, and which selectively causes said RF antenna to vary the designated spatial volume; (G) a second receiver which is located remote from said bed and which detects the presence or absence of said second signal, thereby detecting whether or not said designated anatomical part of said person is located within said designated spatial volume; and (H) an alarm generator which is coupled to said second receiver and which generates an alarm signal wherever said second receiver receives said second signal.

* * * * *

UNITED STATES PATENT AND TRADEMARK OFFICE
CERTIFICATE OF CORRECTION

PATENT NO. : 5,519,380
DATED : May 21, 1996
INVENTOR(S) : Donald A. Edwards

It is certified that error appears in the above-indentified patent and that said Letters Patent is hereby corrected as shown below:

Column 14, Line 2, delete "pan" and substitute --part--.
Column 14, Line 3, delete "signals" and substitute --signal--.
Column 14, Line 28, delete "controller" and substitute --control module--.
Column 14, Line 51, after "unless" insert --said--; and delete "signals" and substitute --signal--.
Column 15, Line 51, delete "pan" and substitute --part--.
Column 15, Line 62, delete "d" and substitute --of--.
Column 16, Line 22, delete "encompassing" and substitute --encompasses--.
Column 16, Line 36, delete "pan" and substitute --part--.
Column 16, Line 41, delete "said" and substitute --a--.
Column 16, Line 50-51, delete "further comprising" and substitute --wherein said--.
Column 16, Line 51, after "means" delete "," and substitute --is--.
Column 16, Line 52, after "receiver" delete ", for setting" and substitute --and sets--.
Column 16, Line 66, after "of" delete "h" and subsitute --a--.
Column 17, Line 4, after "said" delete "tint" and substitute --first--.
Column 18, Line 11, after "signal" delete "wherever" and substitute --whenever--.

Signed and Sealed this

Tenth Day of September, 1996

Attest:

BRUCE LEHMAN

Attesting Officer        Commissioner of Patents and Trademarks